United States Patent
Baccelli et al.

(10) Patent No.: US 9,949,778 B2
(45) Date of Patent: Apr. 24, 2018

(54) SPINAL IMPLANT WITH FLEXIBLE TIE

(75) Inventors: Christian Baccelli, Saucats (FR); Régis Le Couedic, Andresy (FR); Keyvan Mazda, Paris (FR)

(73) Assignee: Zimmer Spine S.A.S., Bordeaux (FR)

( * ) Notice: Subject to any disclaimer, the term of this patent is extended or adjusted under 35 U.S.C. 154(b) by 875 days.

(21) Appl. No.: 13/154,257

(22) Filed: Jun. 6, 2011

(65) Prior Publication Data

US 2011/0238118 A1 Sep. 29, 2011

Related U.S. Application Data

(63) Continuation of application No. 12/408,592, filed on Mar. 20, 2009, which is a continuation of application (Continued)

(30) Foreign Application Priority Data

Sep. 21, 2005 (FR) ..................... 05 09629

(51) Int. Cl.
*A61B 17/70* (2006.01)
*A61B 17/88* (2006.01)
*A61B 17/84* (2006.01)

(52) U.S. Cl.
CPC ...... *A61B 17/8861* (2013.01); *A61B 17/8869* (2013.01); *A61B 17/7053* (2013.01); *A61B 17/7062* (2013.01); *A61B 17/842* (2013.01)

(58) Field of Classification Search
CPC ............ A61B 17/7053; A61B 17/7062; A61B 17/842

(Continued)

(56) References Cited

U.S. PATENT DOCUMENTS 902,040 A 10/1908 Wyckoff
1,346,940 A 7/1920 Collins
(Continued)

FOREIGN PATENT DOCUMENTS

DE 19716504 12/1998
EP 0780096 6/1997
(Continued)

OTHER PUBLICATIONS

Notice of Allowance issued in U.S. Appl. No. 11/996,918, dated Dec. 19, 2011, 9 pages.
(Continued)

*Primary Examiner* — Jan Christopher Merene
*Assistant Examiner* — Atiya Mahmud
(74) *Attorney, Agent, or Firm* — Schwegman Lundberg & Woessner, P.A.

(57) ABSTRACT

A spinal implant can be fastened on a bony element of a patient via a flexible tie. In some embodiments, the spinal implant has two jaws, each having a recess and an opening. The recess is configured to receive a portion of a rod. A portion of the flexible tie is passed through the opening and between a wall of the recess and a surface of the rod to form a loop that can be placed around the bony element. The two jaws are hinged at one end and engaged at the opposite end via a locking member. The locking member can be adjusted to simultaneously hold the jaws together in a fixed position relative to the rod and lock the flexible tie, which has been properly tensioned, in translation relative to the spinal implant.

13 Claims, 3 Drawing Sheets

Related U.S. Application Data

No. 11/996,918, filed as application No. PCT/FR2006/050909 on Sep. 20, 2006.

(58) Field of Classification Search
USPC ......... 606/248, 249, 263, 74, 277, 278, 319, 606/324, 305–308, 264–272; 623/17.11, 623/17.15
See application file for complete search history.

(56) References Cited

U.S. PATENT DOCUMENTS

| | | | |
|---|---|---|---|
| 2,049,361 | A | 7/1936 | Johan |
| 3,834,395 | A * | 9/1974 | Santos .................... 606/139 |
| 4,570,618 | A | 2/1986 | Wu |
| 5,030,220 | A | 7/1991 | Howland |
| 5,304,178 | A | 4/1994 | Stahurski |
| 5,356,412 | A | 10/1994 | Golds et al. |
| 5,413,576 | A | 5/1995 | Rivard |
| 5,449,361 | A | 9/1995 | Preissman |
| 5,480,406 | A * | 1/1996 | Nolan et al. .................. 606/139 |
| 5,496,318 | A * | 3/1996 | Howland et al. ............ 606/249 |
| 5,609,634 | A | 3/1997 | Voydeville |
| 5,662,653 | A * | 9/1997 | Songer et al. ................ 606/270 |
| 5,667,508 | A | 9/1997 | Errico |
| 5,669,917 | A | 9/1997 | Sauer et al. |
| 5,693,061 | A * | 12/1997 | Pierce et al. .................. 606/198 |
| 5,702,399 | A | 12/1997 | Kilpeta et al. |
| 5,720,751 | A | 2/1998 | Jackson |
| 5,772,663 | A | 6/1998 | Whiteside et al. |
| RE36,221 | E | 6/1999 | Breard |
| 5,935,133 | A | 8/1999 | Wagner et al. |
| 5,938,663 | A | 8/1999 | Petreto |
| 5,964,769 | A | 10/1999 | Wagner et al. |
| 6,053,921 | A | 4/2000 | Wagner et al. |
| 6,086,590 | A * | 7/2000 | Margulies et al. ........... 606/263 |
| 6,099,527 | A | 8/2000 | Hochschuler et al. |
| 6,146,386 | A | 11/2000 | Blackman et al. |
| 6,179,838 | B1 | 1/2001 | Fiz |
| 6,228,096 | B1 | 5/2001 | Marchand |
| 6,241,740 | B1 | 6/2001 | Davis et al. |
| 6,277,120 | B1 | 8/2001 | Lawson |
| 6,299,613 | B1 | 10/2001 | Ogilvie et al. |
| 6,309,390 | B1 | 10/2001 | Le Couedic et al. |
| 6,325,802 | B1 * | 12/2001 | Frigg ............................ 606/263 |
| 6,352,557 | B1 | 3/2002 | Ferree |
| 6,391,030 | B1 | 5/2002 | Wagner et al. |
| 6,419,702 | B1 | 7/2002 | Ferree |
| 6,447,518 | B1 | 9/2002 | Krause et al. |
| 6,478,798 | B1 | 11/2002 | Howland |
| 6,514,255 | B1 | 2/2003 | Ferree |
| 6,547,770 | B2 | 4/2003 | Carlsson et al. |
| 6,547,790 | B2 | 4/2003 | Harkey, III et al. |
| 6,569,164 | B1 | 5/2003 | Assaker et al. |
| 6,569,171 | B2 | 5/2003 | DeGuillebon et al. |
| 6,605,091 | B1 | 8/2003 | Iwanski |
| 6,616,669 | B2 | 9/2003 | Ogilvie et al. |
| 6,656,179 | B1 | 12/2003 | Schaefer et al. |
| 6,656,185 | B2 | 12/2003 | Gleason et al. |
| 6,682,533 | B1 | 1/2004 | Dinsdale et al. |
| 6,689,140 | B2 | 2/2004 | Cohen |
| 6,695,852 | B2 | 2/2004 | Gleason |
| 6,723,335 | B1 | 4/2004 | Moehlenbruck et al. |
| 6,746,452 | B2 | 6/2004 | Tuke et al. |
| 6,773,438 | B1 | 8/2004 | Knodel et al. |
| 6,946,000 | B2 | 9/2005 | Senegas et al. |
| 7,481,828 | B2 | 1/2009 | Mazda et al. |
| 7,699,874 | B2 | 4/2010 | Young |
| 7,959,654 | B2 | 6/2011 | Mazda et al. |
| 2002/0082600 | A1* | 6/2002 | Shaolian et al. .............. 606/61 |
| 2002/0116013 | A1* | 8/2002 | Gleason et al. .............. 606/151 |
| 2002/0198538 | A1 | 12/2002 | Kortenbach et al. |
| 2003/0004511 | A1* | 1/2003 | Ferree ............................. 606/61 |
| 2003/0195628 | A1 | 10/2003 | Bao et al. |
| 2004/0087979 | A1 | 5/2004 | Field et al. |
| 2004/0097942 | A1 | 5/2004 | Allen et al. |
| 2004/0138666 | A1 | 7/2004 | Molz, IV et al. |
| 2005/0070958 | A1 | 3/2005 | Swayze et al. |
| 2005/0085815 | A1 | 4/2005 | Harms |
| 2005/0131404 | A1 | 6/2005 | Mazda |
| 2005/0154403 | A1 | 7/2005 | Sauer et al. |
| 2005/0177156 | A1 | 8/2005 | Timm et al. |
| 2005/0228375 | A1 | 10/2005 | Mazda et al. |
| 2005/0273983 | A1 | 12/2005 | Mattchen |
| 2006/0235387 | A1 | 10/2006 | Peterman |
| 2006/0235391 | A1 | 10/2006 | Sutterlin, III |
| 2007/0016190 | A1 | 1/2007 | Martinez et al. |
| 2007/0088359 | A1 | 4/2007 | Woods et al. |
| 2007/0299445 | A1 | 12/2007 | Shadduck et al. |
| 2008/0033557 | A1 | 2/2008 | Pasquet et al. |
| 2008/0058812 | A1 | 3/2008 | Zehnder |
| 2008/0125780 | A1 | 5/2008 | Ferree |
| 2008/0140133 | A1 | 6/2008 | Allard et al. |
| 2008/0208256 | A1 | 8/2008 | Thramann |
| 2009/0131985 | A1 | 5/2009 | Mazda |
| 2009/0138048 | A1 | 5/2009 | Baccelli et al. |
| 2009/0326585 | A1 | 12/2009 | Baccelli et al. |
| 2011/0034956 | A1 | 2/2011 | Mazda et al. |
| 2012/0022591 | A1 | 1/2012 | Baccelli et al. |

FOREIGN PATENT DOCUMENTS

| | | |
|---|---|---|
| EP | 1815812 | 8/2007 |
| FR | 522040 | 7/1921 |
| FR | 26156 | 9/1932 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| FR | 2897771 A1 | 8/2007 |
| GB | 2269753 | 2/2004 |
| JP | 2001299770 | 10/2001 |
| WO | WO199416635 A1 | 8/1994 |
| WO | 0154599 A1 | 8/2001 |
| WO | WO200207621 A1 | 1/2002 |
| WO | WO200207622 A1 | 1/2002 |
| WO | 2002009604 A1 | 2/2002 |
| WO | WO0209604 * | 2/2002 |
| WO | WO200209604 A1 | 2/2002 |
| WO | WO200217803 A2 | 3/2002 |
| WO | WO2002051326 A1 | 7/2002 |
| WO | WO2002071960 A1 | 9/2002 |
| WO | WO 2003007829 A1 | 1/2003 |
| WO | WO2003103519 A1 | 12/2003 |
| WO | WO2004010881 A1 | 2/2004 |
| WO | WO 2005020860 A3 | 3/2005 |
| WO | WO2005120277 A1 | 12/2005 |
| WO | WO2006034423 A2 | 3/2006 |
| WO | WO 2006106268 A3 | 10/2006 |
| WO | WO 2006106246 | 12/2006 |
| WO | WO 2007023240 A3 | 3/2007 |
| WO | WO2007034112 A1 | 3/2007 |
| WO | WO 200736657 | 4/2007 |
| WO | WO2007099258 A2 | 9/2007 |
| WO | WO2009130276 A1 | 10/2009 |
| WO | WO2009141393 A1 | 11/2009 |

OTHER PUBLICATIONS

Notice of Allowance issued in U.S. Appl. No. 11/877,160, dated Oct. 31, 2011, 7 pages.
Office Action issued in U.S. Appl. No. 12/408,592, dated Sep. 22, 2011, 24 pages.
Office Action issued in U.S. Appl. No. 12/059,634, dated Oct. 5, 2011, 12 pages.
European Search Report issued in European Patent Application No. EP 08305124.3, 3 pages.
English Translation of International Preliminary Report issued in International Patent Application No. PCT/FR2006/050898 on Patentability Chapter I dated Apr. 29, 2008, 6 pages.

(56) References Cited

OTHER PUBLICATIONS

English Translation of International Preliminary Report on Patentability Chapter I issued in International Patent Application No. PCT/FR2006/ 050909 dated Apr. 8, 2008, 5 pages
English Translation of the Written Opinion of the International Search Authority issued in International Patent Application No. PCT/FR2006/ 050909 dated Apr. 2, 2008, 4 pages
English Translation of the Written Opinion of the International Search Authority issued in International Patent Application No. PCT/FR2006/050898 dated Apr. 28, 2008, 5 pages
European Search Report issued in European Patent Application No. EP 08305183 dated Mar. 19, 2009, 10 pages
European Search Report issued in European Patent Application No. EP 08305326 dated Nov. 12, 2008, 3 pages
European Search Report issued in European Patent Application No. EP 2052689 dated Apr. 15, 2008, 6 pages
European Search Report issued in European Patent Application No. EP08305326 dated Nov. 18, 2006, 3 pages
French Preliminary Search Report and Written Opinion in French Patent Application No. FR200650609 dated Jun. 30, 2006, 5 pages
International Search Report issued in International Patent Application No. WO2009053423 dated May 19, 2009, 4 pages
International Search Report issued in International Patent Application No. PCT/EP2008/063682, dated Nov. 24, 2008 3 pages
International Search Report Issued in International Patent Application No. PCT/FR2006/050909, published as WO/2007/034112, dated Jan. 24, 2007, 3 pages
Office Action issued in U.S. Appl. No. 10/521,914 dated Dec. 29, 2006, 21 pages
Office Action issued in U.S. Appl. No. 10/521,914 dated Mar. 19, 2008, 7 pages
Office Action issued in U.S. Appl. No. 10/521,914 dated Jun. 16, 2006, 13 pages
Office Action issued in U.S. Appl. No. 10/521,914 dated Jul. 30, 2007, 13 pages
International Search Report and Written Opinion issued in International Patent Application No. PCT/US2009/038977 dated Jul. 22, 2009, 13 pages
Korean Examination report issued in Korean Patent Application No. 1020057001238 dated Feb. 23, 2010, 3 pages
French Preliminary Search Report issued in French Patent Application No. FR0209317 dated Apr. 9, 2003, 1 page.
French Preliminary Search Report issued in French Patent Application No. FR0509629 dated Jun. 9, 2006, 2 pages
International Search Report issued in International Patent Application No. PCT/FR2003/02307 dated Jan. 2, 2004, 2 pages
Australian Search Report issued in Australian Patent Application No. 2003267529 dated Nov. 15, 2007, 2 pages
French Preliminary Search Report issued in French Patent Application No. FR0509570 dated Jun. 29, 2006, 2 pages
International Search Report issued in International Patent Application No. PCT/FR2006/050898 dated Feb. 2, 2007, 2 pages
Written Opinion issued in International Patent Application No. PCT/US2009/038977 dated Feb. 24, 2010, 7 pages
European Search Report issued in European Patent Application No. 07 301 454.0, dated Sep. 25, 2008, 8 pages.
Partial European Search Report issued in European Patent Application No. 07 301 483.9, completed Apr. 15, 2008, dated Apr. 23, 2008, 6 pages
European Search Report and Search Opinion issued in European Patent Application No. 07 301 483.9, completed Apr. 15, 2008, dated Jul. 10, 2008, 10 pages
International Search Report and Written Opinion issued in International Patent Application No. PCT/EP2008/064344, completed Jan. 16, 2009, dated May 19, 2009, 11 pages
International Search Report and Written Opinion issued in International Patent Application No. PCT/EP2008/062791, completed Nov. 18, 2008, dated Dec. 4, 2008, 10 pages
French Preliminary Search Report issued in French Patent Application No. 0757814, dated May 22, 2008, 2 pages
International Preliminary Report on Patentability issued in International Patent Application No. PCT/ EP2008/062791, dated Mar. 30, 2010, 7 pages
International Preliminary Report on Patentability issued in International Patent Application No. PCT/ EP2008/063682, dated Apr. 13, 2010, 8 pages
International Preliminary Report on Patentability issued in International Patent Application No. PCT/ EP2008/064344, dated Apr. 27, 2010, 8 pages
International Preliminary Report on Patentability issued in International Patent Application No. PCT/US2009/038977, dated May 27, 2010, 12 pages
French Preliminary Search Report issued in French Patent Application No. FR 0405611, dated Jan. 12, 2005, 2 pages
International Search Report issued in International Patent Application No. PCT/FR2005/001280, dated Nov. 7, 2005, 3 pages
Written Opinion issued in International Patent Application No. PCT/FR2005/001280, dated Nov. 25, 2006, 5 pages
International Search Report issued in International Patent Application No. PCT/EP2008/064344, published as WO/2008/053423, dated May 19, 2009, 5 pages
International Search Report and Written Opinion issued in International Patent Application No. PCT/EP2008/063682, dated Nov. 24, 2008, 11 pages
International Search Report and Written Opinion issued in International Patent Application No. PCT/FR2006/050909, published as WO/2007/034112, dated Jan. 24, 2007, 10 pages
Office Action issued in U.S. Appl. No. 12/358,748, dated Sep. 15, 2010, 7 pages
Office Action issued in U.S. Appl. No. 11/877,160, dated Nov. 26, 2010, 10 pages
Office Action issued in U.S. Appl. No. 11/996,918, dated Feb. 14, 2011, 12 pages
Office Action issued in U.S. Appl. No. 12/059,634, dated Feb. 15, 2011, 15 pages
Office Action issued in U.S. Appl. No. 12/408,592, dated Feb. 18, 2011, 17 pages
Notice of Allowance issued in U.S. Appl. No. 12/358,748, dated Feb. 23, 2011, 5 pages
Office Action issued in U.S. Appl. No. 11/877,160, dated Apr. 12, 2011, 12 pages.
Office Action issued in U.S. Appl. No. 12/059,634, dated Jun. 22, 2011, 15 pages
European Search Report issued in European Patent Application No. EP08305124.3, dated Oct. 24, 2008, 4 pages
Office Action issued in U.S. Appl. No. 11/996,918, dated Aug. 17, 2011, 11 pages
Notice of Allowance issued in U.S. Appl. No. 12/375,265, dated Aug. 25, 2011, 10 pages.

* cited by examiner

SPINAL IMPLANT WITH FLEXIBLE TIE

CROSS-REFERENCE TO RELATED APPLICATIONS

This application is a continuation of and claims a benefit of priority under 35 U.S.C. § 120 from U.S. patent application Ser. No. 12/408,592, filed Mar. 20, 2009, entitled "FLEXIBLE TIE FASTENING SYSTEM," which is a continuation of and claims priority from U.S. patent application Ser. No. 11/996,918, filed Jan. 25, 2008, entitled "AN INSTRUMENT FOR TENSIONING A FLEXIBLE TIE," which is the National Stage of International Application No. PCT/FR2006/050909, filed Sep. 20, 2006, which claims priority from French Patent Application No. 0509629, filed on Sep. 21, 2005. This application also relates to U.S. patent application Ser. No. 13/154,983, filed Jun. 7, 2011, entitled "METHOD AND INSTRUMENT FOR TENSIONING A FLEXIBLE TIE." The content of each application referenced herein is hereby incorporated as if fully set forth herein.

TECHNICAL FIELD OF THE INVENTION

The invention relates to a spinal implant that can be fastened on a bony element via a flexible tie.

BACKGROUND OF THE RELATED ART

The spine is made up of a superposition of vertebrae, that are normally aligned along a vertebral axis, going from the lumbar vertebrae to the cervical vertebrae, with each vertebra presenting a posterior wall from which there projects a spinous process and two side edges having walls from which there project the ribs and/or transverse processes. When an individual's spine presents abnormal curvature, the vertebrae are inclined relative to one another and relative to said vertebral axis. The lateral edges of the vertebrae situated on one side are thus closer to one another and form a concave curve, while the lateral edges on the other side appear spaced apart from one another and form a convex curve.

In order to straighten the spinal column, the lateral edges of the vertebrae on the concave side are spaced apart from one another and are taken relative to one another to a distance that is substantially equivalent to the distance between the lateral edges on the other side. Thereafter, in order to keep the vertebrae in that position relative to one another, known devices are used that have screws for insertion into the vertebrae or hooks for inserting along the inside wall of the spinal canal, associated with rods for interconnecting the screws or the hooks.

SUMMARY OF THE INVENTION

The hooks are generally inserted in pairs in each vertebra and on either side close to the pedicles, the heads of the hooks projecting from the posterior wall of a vertebra, one on either side of the spinous process. The heads may be tulip-shaped, for example, and they are suitable for receiving a rod which is secured by means of a nut screwed onto the head and bearing against the rod. Rows constituted by the heads of the hooks situated on either side of the spinous processes are interconnected and held in fixed position by two rods that are parallel to each other and to the axis of the spine.

Nevertheless, using such hooks is tricky, since under no circumstances must the operator harm the spinal cord that extends in the center of the spinal canal, since that would lead to paralysis for the patient.

The use of screws makes it possible to reduce the risks of such surgery. They likewise have tulip-shaped heads and they are inserted in pairs in the posterior walls of vertebrae in the pedicles on either side of the spinous processes. Thus, the screws constitute fastening points in the vertebrae for holding them relative to one another. Nevertheless, the screws are necessarily inserted into the pedicles of the vertebrae, and under certain circumstances, the pedicles may be small in size or they may be damaged.

A problem which arises, and which the invention seeks to solve, is how to obtain such fastening points when it is not possible to introduce screws into the vertebrae in the curved portion, and when using hooks would be too dangerous.

In PCT patent application WO 2004/010881 in the name of the Applicant, a vertebral fastener system is described that enables this problem to be solved.

That vertebral fastener system suitable for mounting on a vertebra of the spine for connection to a rod comprises:

a connection piece disposed facing said rib and/or said transverse process, and suitable for being connected to said rod;

a flexible tie of elongate shape suitable for connecting together said connection piece and at least one rib and/or transverse process; and adjustable locking means secured to said connection piece, said tie presenting a first end secured to said connection piece and a free second end suitable for sliding in said connection piece and to form a loop, said locking means being suitable for simultaneously holding said connection piece in a fixed position relative to the rod and a portion of said tie extending between said ends being suitable for being locked in translation relative to said connection piece by said adjustable locking means, whereby the loop presents a length that is determined in such a manner as to prevent relative displacement of said rod and of said vertebra in opposite directions.

Other flexible tie systems for fastening to a vertebra can be used. This applies in particular to the system shown in accompanying FIG. 1.

It comprises a connection piece 12 constituted by two jaws 20 and 22 that are hinged together at one end about an axis 24. The two jaws have recesses enabling a rod 18 to be put into place and allowing a braid or tie 14 to pass through, the tie forming a loop 28 on one side of the connection piece 12 and two free ends 30 and 32 on the other side of said piece. The connection system also has a locking member constituted by a screw 16 that can be engaged in the ends of the jaws 20 and 22 remote from their hinged ends. The portions of the tie 14 that are engaged in the recesses are secured to the connection piece by being pinched between the walls of the recesses in the connection piece and the rod 18 when the locking screw 16 is fully tightened.

It can be understood that in order to ensure that said assembly is properly fastened on a transverse process, on a rib, or on a portion of the posterior arc of a vertebra, it is necessary to exert tension on the free ends 30 and 32 of the tie 14.

It will also be understood that with the first-described fastener system, it is also necessary to exert tension on the single free end of the tie in order to ensure correct fastening on the bony element.

U.S. Pat. No. 5,964,769 discloses a device serving to exert tension on a cable used for fastening a medical device on a bone. That device presents the drawbacks of acting directly on the tie-tightening device and no disposition allows the tension exerted on the tie to be controlled.

An object of the invention is to provide an instrument for tensioning a flexible tie of an implant that ensures that it is tensioned effectively while nevertheless being easy for the surgeon to use.

To achieve this object, the invention provides an instrument for tensioning a flexible tie used for fastening an implant onto a bony element of a patient by forming a first loop around the bony element, said tie presenting at least one end that projects out from said implant, and said instrument comprises:
- a rod having a first end provided with bearing means for bearing against said implant;
- a moving part that is movable in translation and that surrounds said rod over a fraction of its length;
- holder means for holding the end of said tie, said holder means being connected to said moving part by a dynamometer system; and
- control means mounted on said moving part to cause the moving part to move relative to said rod, thereby tending to move the first end of the rod away from said moving part, thereby exerting tension on said tie relative to said implant.

It will be understood that since the rod bears against the implant, the moving part is secured either to the second loop of the tie, or to the free end of said tie serves to exert tension on said tie, thereby ensuring appropriate tightening of the first loop of the tie on the bony element.

In addition, when the surgeon acts on the control means, the surgeon knows when the appropriate tension has been applied, thus making it possible to avoid untimely breaking of the tie or damage to the bony element.

Preferably, the instrument further comprises an anti-return system for temporarily preventing said rod and said moving part moving in translation relative to each other, in the absence of action on the control means.

Preferably, the dynamometer system comprises a carriage that is movable in translation relative to the rod and to the moving part, said tie-holder stud being secured to said carriage, and a compression spring being interposed between said carriage and a portion of the moving part.

Also preferably, the control means comprise a trigger mounted to pivot relative to the moving part and presenting a manual actuator portion and a finger that acts on said rod.

Also preferably, the instrument further comprises a handle secured to said moving part and disposed in such a manner that the user can grasp said trigger and said handle simultaneously.

BRIEF DESCRIPTION OF THE DRAWINGS

Other characteristics and advantages of the invention appear better on reading the following description of an embodiment of the invention given by way of non-limiting example. The description refers to the accompanying figures, in which.

DETAILED DESCRIPTION

Figure 2:
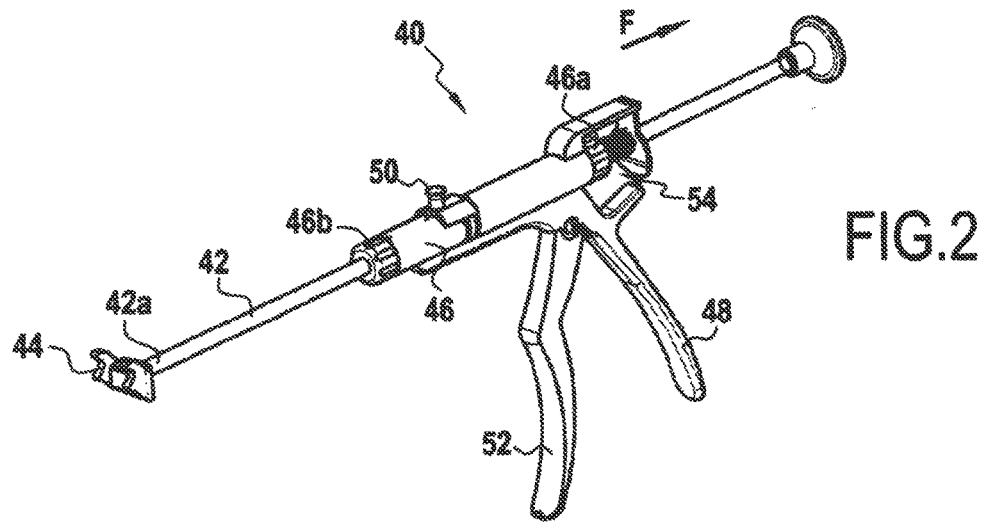
FIG. 2 is a perspective view of the instrument assembly of the invention.

With reference initially to FIG. 2, there follows a description of the instrument assembly 40. It is essentially constituted by a rod 42 having a first end 42a fitted with bearing means 44 for bearing against the implant on which the tie is to be tensioned. The instrument 40 also has a moving part 46 that is movable in translation relative to the rod 42. The moving part 46 is generally cylindrical in shape and is provided with a handle 48. The moving part 46 also has a stud 50 on its portion remote from the handle 48. As explained below, the stud 50 serves to hold the tie on which tension is to be applied. The instrument 40 also comprises a control member constituted by a trigger 52. As explained below, actuating the trigger 52 serves to cause the moving part 46 to move rearwards relative to the rod 42 in the direction of arrow F. In addition, at its end 46a opposite from its end 46b closest to the bearing element 44, the moving part 46 is fitted with an anti-return system acting on the rod 42. As explained in greater detail below, the anti-return system 54 enables the rod 42 and the moving part 46 to be held together temporarily in translation so long as no action is exerted on the trigger 52.

Figure 1:
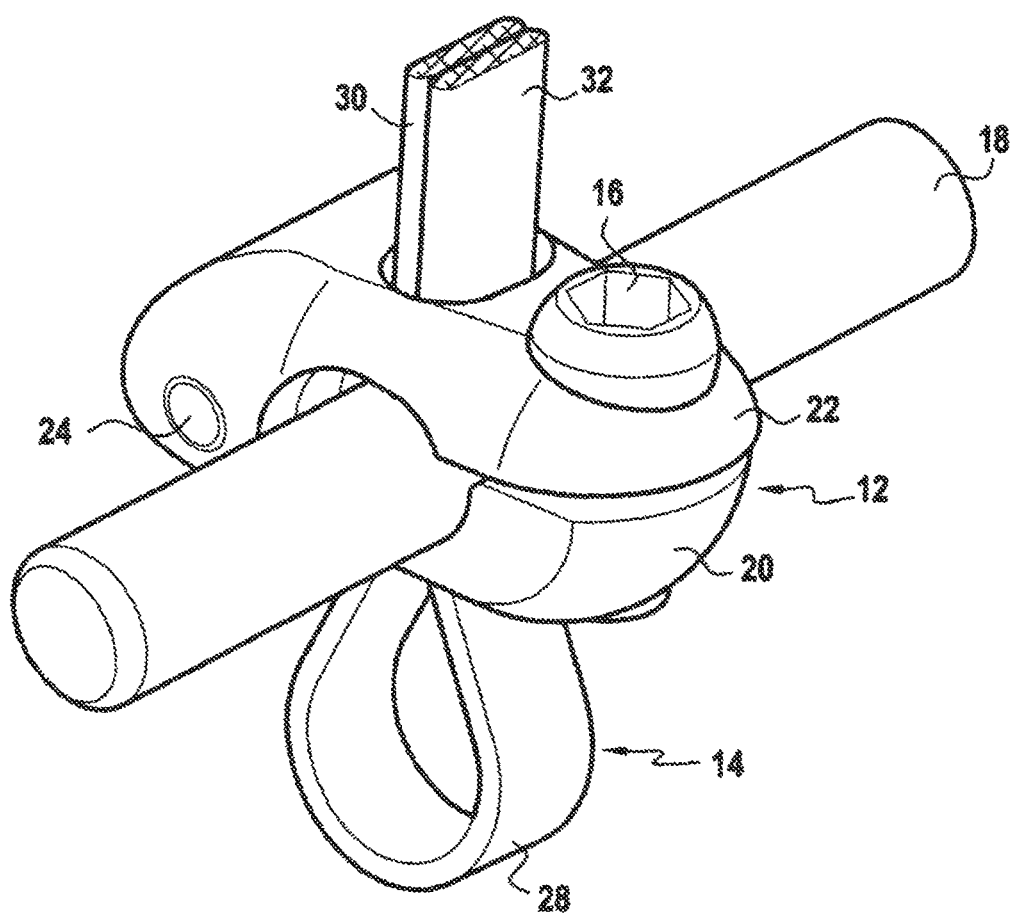
FIG. 1, described above, shows an example of an implant with a fastener tie with which the instrument of the invention can advantageously be used.
Figure 4:
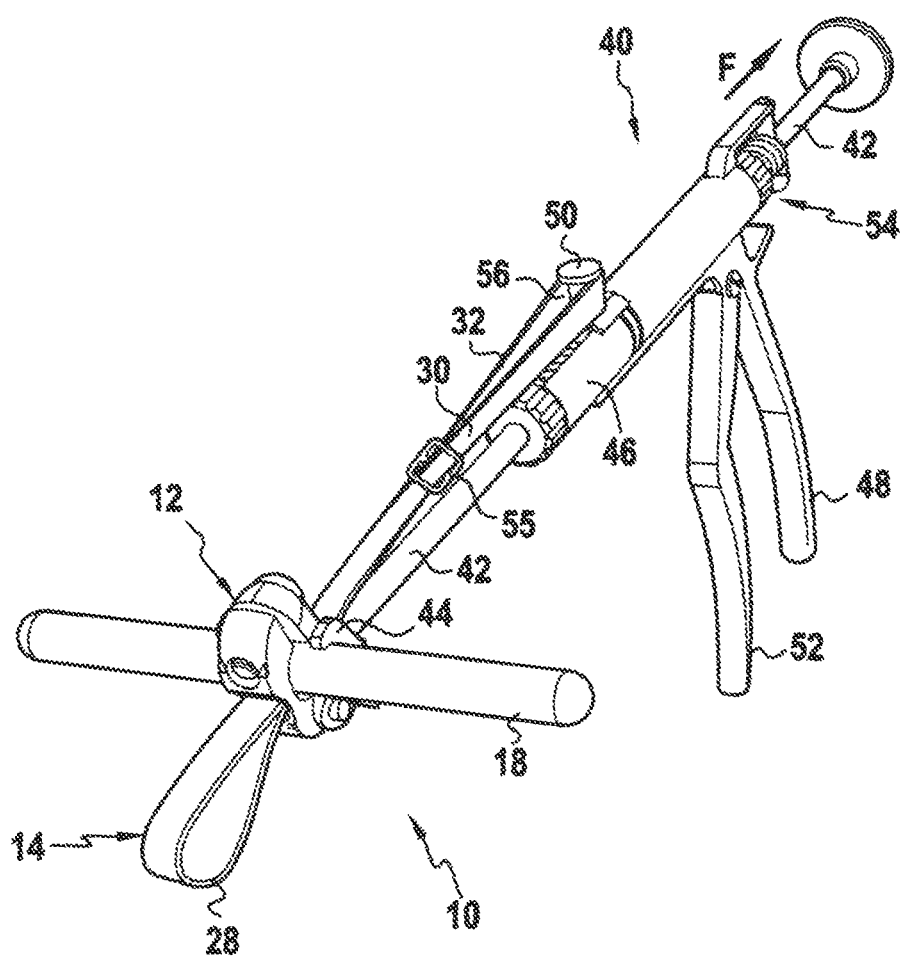
FIG. 4 is a perspective view showing the instrument in use with an implant of the type shown in FIG. 1.

With reference more particularly to FIG. 4, there follows a description in general terms of how the instrument 40 is used. In this figure, there can be seen a vertebral fastener system 10 of the type shown in FIG. 1. In this figure, there can be seen the rod 18, the connection piece 12, and the first fastener loop 28 formed by the tie 14 of the fastener system. This figure also shows that the free end 32 of the tie 14 is connected to the other free end 30 of the same tie by a fastener element 55 of suitable type. Thus, the tie 14 forms a second loop 56.

In use, the bearing means 44 of the instrument bear against the rod 18 on either side of the connection piece 12. The second loop 56 of the tie 14 is engaged on the stud 50 of the moving part 46 of the instrument. It will be understood that when the surgeon exerts action by using the trigger 52 and the handle 48, this causes the moving part 46 to move backwards in the direction F relative to the rod 18, thereby applying traction to the tie as a whole, and in particular to its loop 28. The surgeon can exert successive actions on the trigger 52 because of the presence of the anti-return system 54. As explained below, the instrument is preferably also fitted with a dynamometer system that enables the surgeon to see when a suitable tension has been exerted on the tie 14. Once the suitable tension has been exerted, the instrument 40 is separated from the loop 56 in the tie 14, and the portions of the tie 14 that project beyond the connection piece 12 are cut off.

Figure 3:
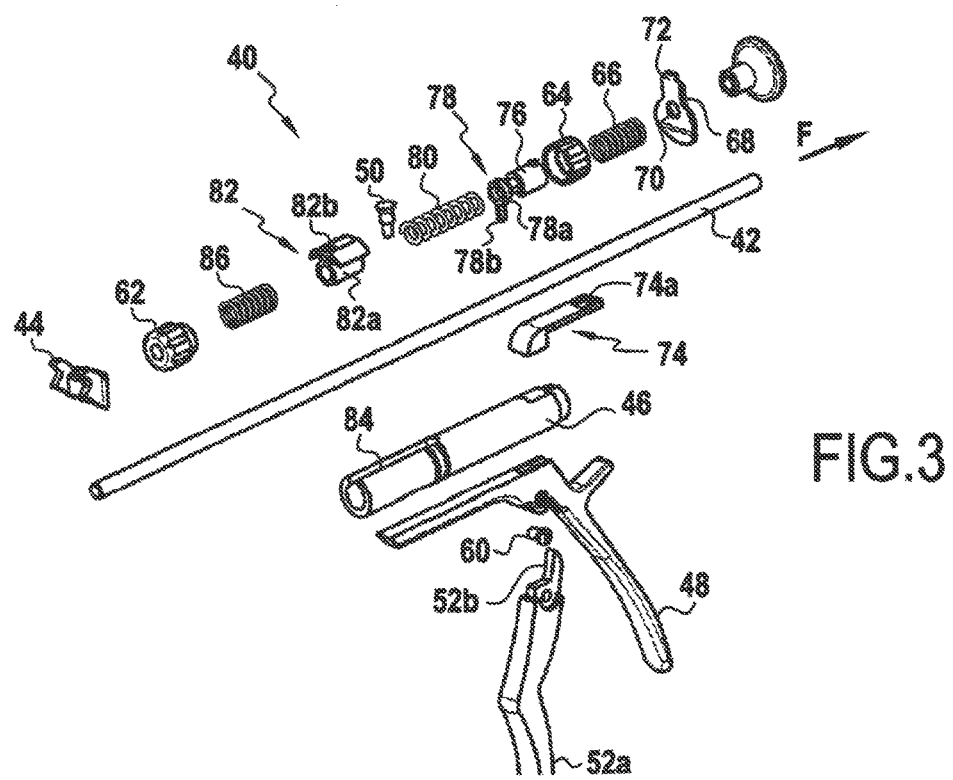
FIG. 3 is an exploded view of the disassembled instrument showing its internal mechanisms.

With reference to FIG. 3, there follows a description in greater detail of the mechanisms of the instrument 40. This figure shows the cylindrically-shaped moving part 46 on which the handle 48 is secured. The trigger 52 is hinged relative to the handle 48 about a pin 60. The trigger 52 has a grip portion 52a and a finger 52b for controlling the rod, for which finger 52b projects beyond the pivot pin 60. The finger 52b penetrates into the moving part 46 via a slot (not shown). The rod 42 is slidably engaged in the moving part 46.

Various elements that are described below are mounted around the rod 42 inside the moving part 46 having open ends that are closed by endpieces 62 and 64 each pierced by an axial bore for passing the rod 42. A spring 66 and a plate 68 constituting the anti-return system are mounted outside the moving part 46, around the rod 42. The plate 68 is pierced by a bore 70 of diameter that is slightly greater than the diameter of the rod. The plate 68 has a tongue 72 that can bear against an arm 74 secured to the rear portion of the moving part 46. Inside the moving part 46 and starting from its end closed by the endpiece 64, there is a spacer cylinder 76, a transmission part 78 constituted by an annular portion 78a and by a stud 78b suitable for co-operating with the finger 52b of the trigger 52. The transmission part 78 is associated with a spring 80. Thereafter there is a carriage 82 having a cylindrical portion 82a engaged around the rod 42 and two external projections 82b. The projections 82b of the carriage 82 are external to the moving part 46 by virtue of a longitudinal slot 84 therein. This external portion of the carriage 82 has the tie-holding stud 50 secured thereto. The carriage 82 is associated with a dynamometer spring 86 which is interposed between the endpiece 62 and the front face of the cylindrical portion 82a of the carriage 82.

In the absence of any action on the trigger 52, the plate 68 of the anti-return system slopes relative to the rod 42 because of the presence of the end 74a of the arm 74, thus causing the rod 42 and the moving part 46 to be temporarily secured to each other in translation. When action is exerted on the trigger 52, the movement of the rod releases the plate 68 and thus allows the rod 42 to move relative to the moving part 46. Similarly, when no action is applied to the trigger 52, the transmission part 78 is free, whereas, in contrast, when action is applied to the trigger 52, the finger 52b acts on the stud 78b of the transmission part 78, thereby temporarily securing it to the rod 42. This temporary connection serves to move the rod 42 relative to the part 46 under the effect of the trigger being actuated.

The dynamometer system operates in simple manner. Under the effect of the rod 42 moving in the direction F relative to the part 46, the dynamometer spring 86 is compressed, causing the carriage 82 to perform relative movement. A mark on the outside face of the moving part 46 makes it possible to detect when the appropriate tension has been applied, this tension corresponding naturally to the dynamometer spring 86 being subjected to predetermined compression.

In the description above, it is assumed that the tie 14 has a second loop used for holding onto the tensioning stud 50 of the instrument. When the tie of the implant has only one free end, this end can be held on the stud 50 or on any other appropriate fastener system so as to exert in the same manner the desired tension on the end of the tie and thus on the loop 28 formed thereby.

What is claimed is:

1. An implant, comprising:
   a flexible tie having a first end portion extending to a first end of the flexible tie, a second end portion extending to a second end of the flexible tie, an intermediate portion, a first portion between the intermediate portion and the first end portion, and a second portion between the intermediate portion and the second end portion;
   a connection piece, wherein the connection piece comprises:
      a passage, wherein the passage is configured to receive a portion of a rod;
      an opening through the connection piece configured for passage of the flexible tie;
      wherein the first and second portions extend through the connection piece such that the intermediate portion of the flexible tie forms a first loop extending outward from a first side of the connection piece and the first and second end portions of the flexible tie are joined together to form a second loop extending outward from a second side of the connection piece, opposite the first side, the second loop configured to be coupled to a tensioning device to apply tension to the first loop of the flexible tie; and
   a locking member, wherein the locking member is configured to lock the first loop of the flexible tie in translation relative to the opening of the connection piece;
   wherein the locking member comprises a screw, and wherein when the locking member is fully tightened by rotating the screw in a first direction, the first and second portions of the flexible tie are pinched between a wall of the connecting piece and a surface of the rod so that the flexible tie is locked in translation relative to the connection piece.

2. An implant according to claim 1, wherein the connection piece includes a first jaw hingedly coupled to a second jaw.

3. An implant according to claim 2, wherein the passage for receiving a portion of the rod is defined between the first and second jaws.

4. A bone fastening system, comprising:
   a flexible tie having a first portion, a second portion, and a third portion extending between the first and second portions; and
   a connecting piece including a first passage for receiving an elongate rod therethrough and a second passage for receiving the first portion and the second portion of the flexible tie therethrough with the third portion of the flexible tie forming a first loop extending outward from a first side of the connecting piece;
   wherein the flexible tie further includes a first free end portion extending from the first portion to a first end of the flexible tie and a second free end portion extending from the second portion to a second end of the flexible tie, the first and second free end portions extending from a second side of the connecting piece and joined together to form a second loop extending outward from the second side of the connecting piece;
   a locking member, wherein the locking member is configured to threadably engage a threaded bore of the connecting piece to hold the connecting piece in a fixed position relative to the rod;
   wherein the locking member does not directly engage the flexible tie when threadably engaged in the threaded bore of the connecting piece;
   wherein the locking member comprises a screw, and wherein when the locking member is fully tightened by rotating the screw in a first direction, the first and second portions of the flexible tie are pinched between a wall of the connecting piece and a surface of the rod so that the flexible tie is locked in translation relative to the connecting piece.

5. A bone fastening system according to claim 4, wherein the connecting piece includes a first jaw hingedly coupled to a second jaw.

6. A bone fastening system according to claim 4, wherein the rod comprises a spinal rod.

7. A bone fastening system according to claim 4, wherein the flexible tie comprises a braid.

8. A bone fastening method, comprising:
   positioning a rod through a first passage of a connecting piece;
   passing a first portion of a flexible tie through a second passage of the connecting piece to form a loop from an intermediate portion of the flexible tie extending outward from the second passage of the connecting piece, wherein the flexible tie further includes a second portion extending through the second passage with the intermediate portion extending between the first and second portions;

wherein the connecting piece includes a first jaw hingedly coupled to a second jaw, wherein each of the first and second jaws further comprises an orifice, and wherein the orifice is configured to receive the flexible tie there-through;

attaching a tensioning tool to a first free end portion of the flexible tie extending from the first portion to a first end of the flexible tie and to a second free end portion of the flexible tie extending from the second portion to a second end of the flexible tie;

tensioning the flexible tie relative to the connecting piece with the tensioning tool; and tightening a locking member in a threaded bore of the connecting piece to hold the connecting piece in a fixed position relative to the rod, wherein the locking member does not contact the flexible tie as the locking member is tightened in the threaded bore of the connecting piece;

wherein the locking member comprises a screw, and wherein tightening the locking member comprises rotating the screw in a first direction to cause the first and second portions of the flexible tie to be pinched between a wall of the connecting piece and a surface of the rod so that the flexible tie is locked in translation relative to the connecting piece.

9. A method according to claim 8, wherein the loop is placed around a bony element.

10. A method according to claim 9, wherein the bony element comprises a transverse process, a rib, or a portion of a posterior arc of a vertebra.

11. A method according to claim 8, wherein the loop is formed on a first side of the connecting piece.

12. A method according to claim 11, wherein the first and second free end portions form a second loop on a second side of the connecting piece opposite the first side.

13. A method according to claim 8, wherein tensioning the flexible tie relative to the connecting piece comprises pulling the first and second free end portions of the flexible tie relative to the connecting piece.

* * * * *